United States Patent [19]

Stults

[11] Patent Number: 5,648,218

[45] Date of Patent: Jul. 15, 1997

[54] PREPARATION OF PHOTOPROTEIN CONJUGATES AND METHODS OF USE THEREOF

[75] Inventor: Nancy L. Stults, Duluth, Ga.

[73] Assignee: SeaLite Sciences, Inc., Norcross, Ga.

[21] Appl. No.: 465,791

[22] Filed: Jun. 6, 1995

Related U.S. Application Data

[63] Continuation-in-part of Ser. No. 293,648, Aug. 22, 1994, Pat. No. 5,486,455, which is a continuation of Ser. No. 117,116, Aug. 13, 1993, abandoned.

[51] Int. Cl.$^6$ .............................. C12Q 1/68; C12Q 1/70; G01N 33/53; C07H 21/04
[52] U.S. Cl. ............................ 435/6; 435/5; 435/7.1; 435/7.2; 435/7.9; 536/26.6; 536/24.3
[58] Field of Search ................... 435/6, 5, 7.1–7.9; 536/26.6, 24.3

[56] References Cited

U.S. PATENT DOCUMENTS

| | | | |
|---|---|---|---|
| 4,396,579 | 8/1983 | Schroeder et al. | 922/52 |
| 4,604,364 | 8/1986 | Kosak | 436/501 |
| 4,608,246 | 8/1986 | Bayer et al. | 435/7.25 |
| 4,657,853 | 4/1987 | Freytag et al. | 435/7.92 |
| 4,665,022 | 5/1987 | Schaeffer et al. | 435/7.72 |
| 4,764,368 | 8/1988 | Blattler et al. | 424/179.1 |
| 4,885,255 | 12/1989 | Stock et al. | 436/512 |
| 4,916,070 | 4/1990 | Matsueda et al. | 530/387.9 |
| 4,925,648 | 5/1990 | Hansen et al. | 424/1.53 |
| 4,927,916 | 5/1990 | Matsueda et al. | 530/387.9 |
| 4,935,339 | 6/1990 | Zahradnik | 435/5 |
| 4,981,979 | 1/1991 | Sivam | 530/391.9 |
| 5,019,393 | 5/1991 | Ito et al. | 424/423 |
| 5,023,181 | 6/1991 | Inouye | 435/189.25 |
| 5,066,789 | 11/1991 | Srinivasan et al. | 530/391.5 |
| 5,087,696 | 2/1992 | Parker et al. | 540/465 |
| 5,093,475 | 3/1992 | Carroll et al. | 530/391.9 |
| 5,094,939 | 3/1992 | Okada et al. | 435/6 |
| 5,098,828 | 3/1992 | Geiger et al. | 435/7.72 |
| 5,112,615 | 5/1992 | Ito et al. | 424/426 |
| 5,116,944 | 5/1992 | Sivam at al. | 530/362 |
| 5,134,071 | 7/1992 | Gaetjens | 435/18 |
| 5,135,736 | 8/1992 | Anderson et al. | 924/1.49 |
| 5,360,728 | 11/1994 | Prasher | 435/189 |

FOREIGN PATENT DOCUMENTS

| | | |
|---|---|---|
| 2-253162 | 10/1990 | Japan . |
| 3-153699 | 7/1991 | Japan . |
| 3-169897 | 7/1991 | Japan . |

OTHER PUBLICATIONS

Tsuji, F.I., Inouye, S., Goto, T. and Sakaki, Y., "Site specific mutagenesis of the calcium binding photoprotein aequorin," *Proc. Natl. Acad. Sci.*, vol. 83, pp. 8107–8111 (1986).

Erikaku, T., Zenno, S., and Inouye, S., "Bioluminescent immunoassay using a monomeric Fab'–photoprotein aequorin conjugate," *Biochem. Biophys. Res. Commun.*, vol. 174, pp. 1331–1336 (1991).

Kurose, K., Inouye, S., Sakaki, Y., and Tsuji, F.I., "Bioluminescence of the Ca#2–binding photoprotein aequorin after cysteine modification," *Proc. Natl. Acad. Sci.*, vol. 86, pp. 80–84 (1989).

Bronstein, I., and McGrath, P., "Chemiluminescence lights up.," *Nature*, vol. 338, pp. 599–600 (1989).

Casadei, J., Powell, M.J. and Kenten, J.H., "Expression and secretion of aequorin as a chimeric antibody by means of a mammalian expression vector," *Proc. Natl. Acad. Sci.*, vol. 87, pp. 2047–2051 (1990).

Zatta, P.F., Smith, D.F., Cormier, M.J., and Cummings, R.D., "A solid phase assay for the evaluation of the glycosylation status of serum glycoproteins using recombinant aequorin," *Proceedings of the VIth International Symposium on Bioluminescence and Chemiluminescence*, Cambridge, England, Sep. 10–13, 1990, pp. 537–540 (1991b).

Zenno, S., and Inouye, S., "Bioluminescent immunoassay using a fusion protein of protein A and the photoprotein aequorin," *Biochem. Biophys. Res. Commun.*, vol. 171, pp. 169–174 (1990).

Means, G.E., Feeney, R.E., "Chemical Modifications if Proteins: History and Applications," *Biocojugate Chem.*, vol. 1, pp. 2–12 (1990).

Prasher et al., "Sequence Comparisons of Complementary DNAs Encoding Aequorin Isotypes," *Biochemistry*, vol. 26, No. 5, pp. 1326–1332 (1987).

Cormier et al., *Photochem. Photobiol.*, vol. 49, pp. 509–512 (1989).

Stults, N.L., Stocks, N. F., Rivera, H., McCann, R.O., O'Kane D., Cummings, R.D., Cormier, M.J., and Smith, D.F., "Use of recombinant biotinylated–aequorin in microtiter and membrane–based assays. Purification of recombinant apoaequorin from *Escherichia coli*," *Biochemistry*, vol. 31, pp. 1433–1442 (1992).

Smith, D.F., Stults, N.L., Rivera, H., Gehle, W.D., Cummings, R.D., and Cormier, M.J., "Applications of recombinant bioluminescent proteins in diagnostic assays," *Proceedings of the VIth International Symposium on Bioluminescence and Chemiluminescence*, Cambridge, England, Sep. 10–13, 1990, pp. 529–532 (1991).

(List continued on next page.)

*Primary Examiner*—Stephanie W. Zitomer
*Assistant Examiner*—Dianne Rees
*Attorney, Agent, or Firm*—Jones & Askew

[57] ABSTRACT

The present invention encompasses a method of synthesis of conjugates of photoproteins that retain all or a substantial portion of the luminescent activity of underivatized photoprotein. According to the present invention photoproteins may be conjugated with a variety of binding reagents including streptavidin/avidin, glycoproteins, lectins, hormones, antigens, drugs, antibodies and antigen binding fragments thereof, or any other selectively bindable reagent by chemical crosslinking means. The present invention also encompasses conjugates produced by this method, and methods of use of such conjugates.

26 Claims, 8 Drawing Sheets

OTHER PUBLICATIONS

Zatta, P.F., Nyame, K., Cormier, M.J., Mattox, S.A., Prieto, P.A., Smith, D.F., and Cummings, R.D., "A solid phase assay for b1,4 galactosyl transferase activity in human serum using recombinant aequorin," *Anal. Biochem.*, vol. 194, pp. 185–191 (1991a).

King, T.P. et al., "Preparation of protein conjugates via intermolecular disulfide bond formation," *Biochemistry*, vol. 17, No. 8, pp. 1499–1506 (1978).

Alter, "Role and Reactivity of fireflys luciferase", Diss. Abs. vol. 46: 9B, p. 3033 1985.

Kemple, M.D., Ray B.D., Jarori, G.K., Nageswara Rao, B.D., and Prendergast, F.G. (1984) Electron paramagnetic resonance of spin–labeled aequorin. *Biochemistry* 23, 4383–4390.

Mengeling, B.J., Smith, P.L., Stults, N.L., Smith D.F., and Baenziger, J. U., "A microplate assay for analysis of solution phase glycosyltransferase reactions: determination of kinetic constants," *Anal. Biochem.*, vol. 199, pp. 286–292 (1991).

Shimomura, O., and Johnson, F.H., "Peroxidized coelenterazine, the active group in the photoprotein aequorin," *Proc. Natl. Acad. Sci.*, vol. 75, pp. 2611–2615 (1978).

Stults, N.L., Stocks, N. F., Cummings, R.D., Cormier, M.J., and Smith, D.F., "Applications of recombinant bioluminescent proteins as probes for proteins and nucleic acids," *Proceedings of the VIth International Symposium on Bioluminescence and Chemiluminescence.*, Cambridge, England, Sep. 10–13, 1990, pp. 533–536 (1991).

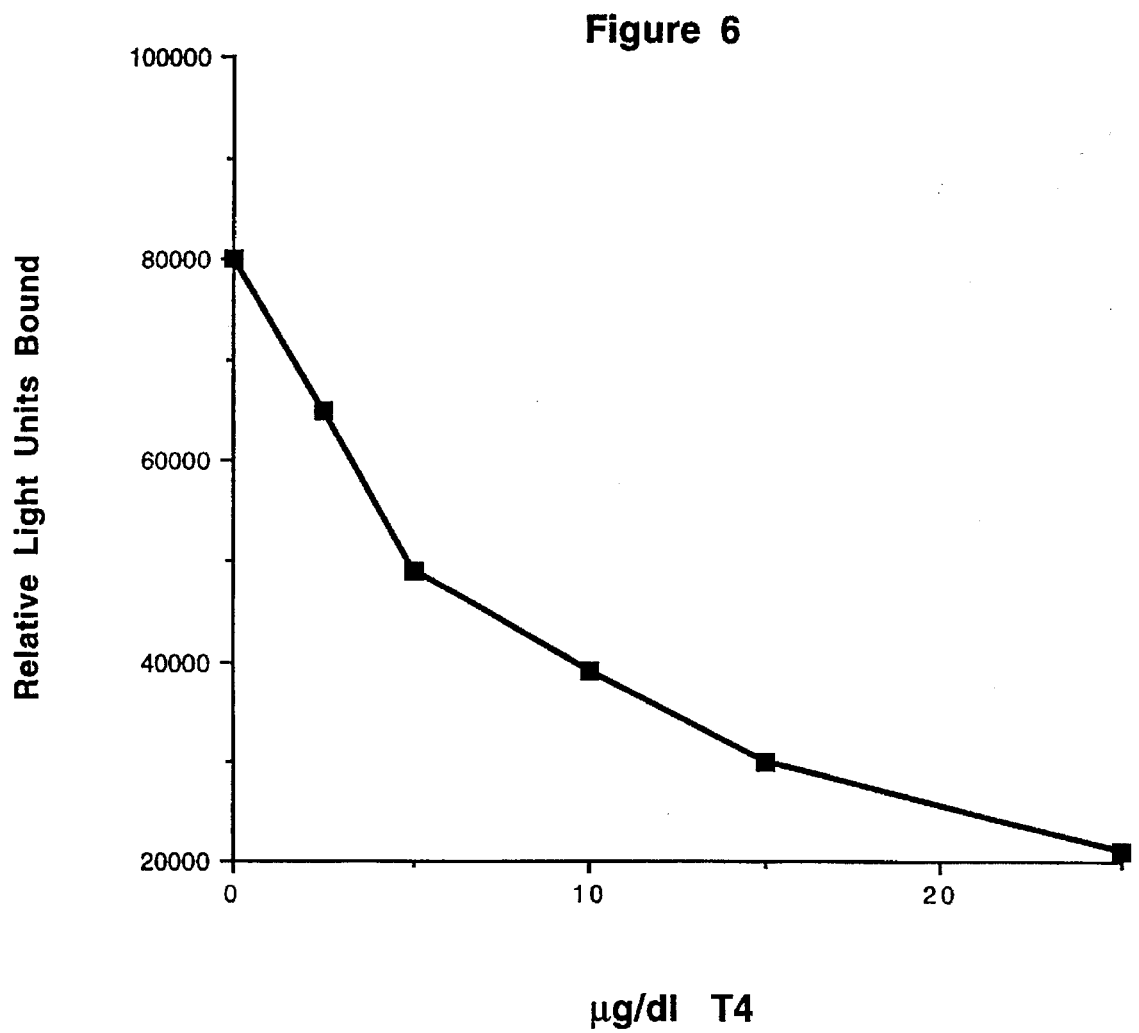

PREPARATION OF PHOTOPROTEIN CONJUGATES AND METHODS OF USE THEREOF

CROSS-REFERENCE TO RELATED APPLICATIONS

This is a continuation-in-part of Ser. No. 08/293,648, filed Aug. 22, 1994, now U.S. Pat. No. 5,486,455, which is a continuation of Ser. No. 08/117,116, filed Feb. 12, 1993, now abandoned.

TECHNICAL FIELD

The invention relates to labeled specific-binding assay reagents, and more particularly to specific-binding assay reagents comprising luminescent proteins coupled to binding molecules.

BACKGROUND OF THE INVENTION

Bioluminescence refers to the emission of light by biological molecules. Bioluminescent proteins can be true enzymes such as luciferases, which catalyze the oxidation of luciferin, emitting light and releasing oxyluciferin, or photoproteins, which catalyze the oxidation of luciferin to emit light but do not release the oxidized substrate. Examples of bioluminescent proteins include those isolated from the ctenophores Mnemiopsis (mnemiopsin) and Beroe ovata (berovin), those isolated from the coelenterates Aequoria (aequorin), Obelia (obelin), Pelagia, and luciferases such as Renilla (*Renilla luciferase*) and those isolated from the molusca Pholas (pholasin). Bioluminescent proteins also can be isolated from ostracods such as Cypridina.

A bioluminescent protein particularly useful as a label in diagnostic assays is the photoprotein aequorin. Aequorin catalyzes the oxidation of coelenterate luciferin to oxyluciferin, resulting in the concomitant production of blue light (lambda$_{max}$=469 nm). Aequorin consists of apoaequorin, a single polypeptide chain of M$_r$ 22,000, containing one mole each of tightly bound coelenterate luciferin and oxygen. Light emission from this complex is initiated upon the binding of calcium ions. Aequorin catalyzes a single turnover event or "flash reaction" which persists for approximately 10 seconds.

Due to the relatively high quantum yield of the reaction, aequorin can be detected at the attomol level ($10^{-18}$ mol) using commercially available luminometers. Because of its calcium requirement and ability to be detected at very low levels, aequorin has proven useful for monitoring levels of intracellular calcium. The potential utility of using aequorin as a nonradioisotopic reporter molecule has only recently been realized with the availability of the recombinant protein (reviewed by Cormier et al., Cormier, M. J. Prasher D C Longiatu, M & McCann, R. O. 1989, *Photochem. Photobiol.* 49: 509–512).

Until very recently, it was generally considered in the art that all bioluminescent proteins were inherently unstable and complex, thus making them unsuitable for reporter molecules, based on the properties of firefly *Photinus pyralis* luciferase (Bronstein & McGrath, 1989 Chemiluminescence Lights Up. *Nature* 338, 599–600). However, the biotinylated derivative of aequorin recently has been shown to retain greater than 80 percent of its original activity and, when used in combination with streptavidin, has been demonstrated to detect nanogram to subnanogram amounts of biotinylated targets, including protein antigens and DNA immobilized onto microtiter walls or membrane supports (Stults et al., 1992, Rivera, H., McCann, R. O., O'Kane D., Cummings, R. D., Cormier M. J., Smith D. F. Use of Recombinant Biotinylated-Aequorin in Microtiter and Membrane-Based Assays. Purification of Recombinant Apoaequorin From *Escherichia coli.*, *Biochemistry*, 31, 1433–1442). In addition, biotinylated aequorin also has been successfully used in a capture immunoassay for Salmonella antigen (Smith et al., 1991, A Microplate Assay For Analysis of Solution Phase Glycosyltransferase Reactions: Determination of Kinetic Constants. *Anal. Biochem.* 199, 286–292) and in solid phase assays for glycosyl transferases and glycoproteins (Mengeling et al., 1991, A Microplate Assay For Analysis of Solution Phase Glycosyltransferase Reactions: Determination of Kinetic Constants. *Anal. Biochem.* 199, 286–292), (Zatta et al., 1991, A Solid Phase Assay For β1,4 Galactosyl Transferase Activity in Human Serum Using Recombinant Aequorin, Anal. Biochem. 194, 185–191).

Although the biotinylated derivative of aequorin performs well in a variety of different assay formats, it would be advantageous to synthesize by chemical crosslinking methods direct conjugates of recombinant aequorin with a variety of selectively bindable reagent including receptors, hormones, lectins, antibodies and binding fragments thereof, antigens, DNA, RNA, oligonucleotides, and glycoproteins. Such conjugates would facilitate faster detection of biological targets by reducing the number of incubation steps or by eliminating the avidin/streptavidinobiotin interaction entirely.

Direct chemical crosslinking of apoaequorin to antibody FAB fragments using a heterobifunctional reagent has been reported (Erikaku et al., 1991, Bioluminescent Immunoassay Using a Monomeric Fab'-Photoprotein Aequorin Conjugate. *Biochem. Biophys. Res. Commun.* 174, 1331–1336). The antibody conjugate was prepared using a chemical crosslinking technique based on modification of amino or thiol groups on apoaequorin with maleimido groups. Unfortunately, this crosslinking procedure results in apoaequorin-antibody conjugates that retained about only 10 percent of the activity of underivatized aequorin. (See Abst., p. 1331 Erikaku et al, 1991).

What is needed, therefore, is a direct chemical crosslinking method for preparing photoprotein conjugates that substantially preserves photoprotein activity.

SUMMARY OF THE INVENTION

The present invention encompasses a method of synthesis of conjugates of photoproteins that retain a substantial portion of the luminescent activity of underivatized photoprotein. According to the present invention, photoproteins may be conjugated with a variety of binding reagents including, but not limited to, streptavidin/avidin, lectins, enzymes, glycoproteins, peptides, hormones, receptors, antigens, drugs, antibodies and antigen binding fragments thereof, RNA, DNA, oligonucleotides, or any other selectively bindable molecules or compositions by chemical crosslinking means.

The present invention also encompasses conjugates produced by this method, and methods of use of such conjugates in binding assays to determine the presence and amount in a sample of an analyte. The conjugation method of the present invention includes the steps of introducing additional sulfhydryl groups into a photoprotein to be conjugated, chemically modifying a binding reagent to render it sulfhydryl-reactive, and reacting the sulfhydryl-activated photoprotein with the sulfhydryl-reactive binding reagent to form the photoprotein-binding reagent conjugates of the present invention. The method yields stable photoprotein-binding reagent conjugates that retain luminescent activity.

Accordingly, it is an object, of the present invention to provide a method for producing stable photoprotein-binding reagent conjugates that retain bioluminescent activity.

It is a further object of the present invention to provide stable photoprotein-binding reagent conjugates that retain bioluminescent activity.

It is yet a further object of the present invention to provide a method for the production of stable conjugates of apoaequorin or aequorin that retain bioluminescent activity.

It is a still further object of the present invention to provide stable conjugates of apoaequorin or aequorin which retain bioluminescent activity.

It is yet a further object of the present invention to provide a method whereby binding reagents that contain one or more amino groups may be conjugated to a photoprotein modified to contain at least one additional sulfhydryl group such that the resulting conjugate retains bioluminescent activity.

It is also an object of the present invention to provide stable photoprotein conjugates where the binding reagent is an antibody.

It is also an object of the present invention to provide stable photoprotein conjugates where the binding reagent is an antigen.

It is an object of the present invention to provide stable photoprotein conjugates where the binding reagent is a lectin.

It is another object of the present invention to provide stable photoprotein conjugates where the binding reagent is a receptor.

It is also an object of the present invention to provide stable photoprotein conjugates where the binding reagent is a ligand.

It is also an object of the present invention to provide stable photoprotein conjugates where the binding reagent is an oligonucleotide.

These and other objects, features and advantages of the present invention will become apparent after a review of the following detailed description of the disclosed embodiment and the appended claims.

BRIEF DESCRIPTION OF THE FIGURES

FIG. 6 is the graphic representation of the binding of an aequorin-thyroxine (T4) conjugate versus thyroxine (T4) in a competitive immunoassay.

FIG. 7A: HPLC size exclusive chromatography of obelin anti-TSH antibody conjugate reaction mixture. FIG. 7B: HPLC DEAE ion exchange chromatography of obelin conjugate peak from sec. column.

DETAILED DESCRIPTION OF THE INVENTION

Figure 1:
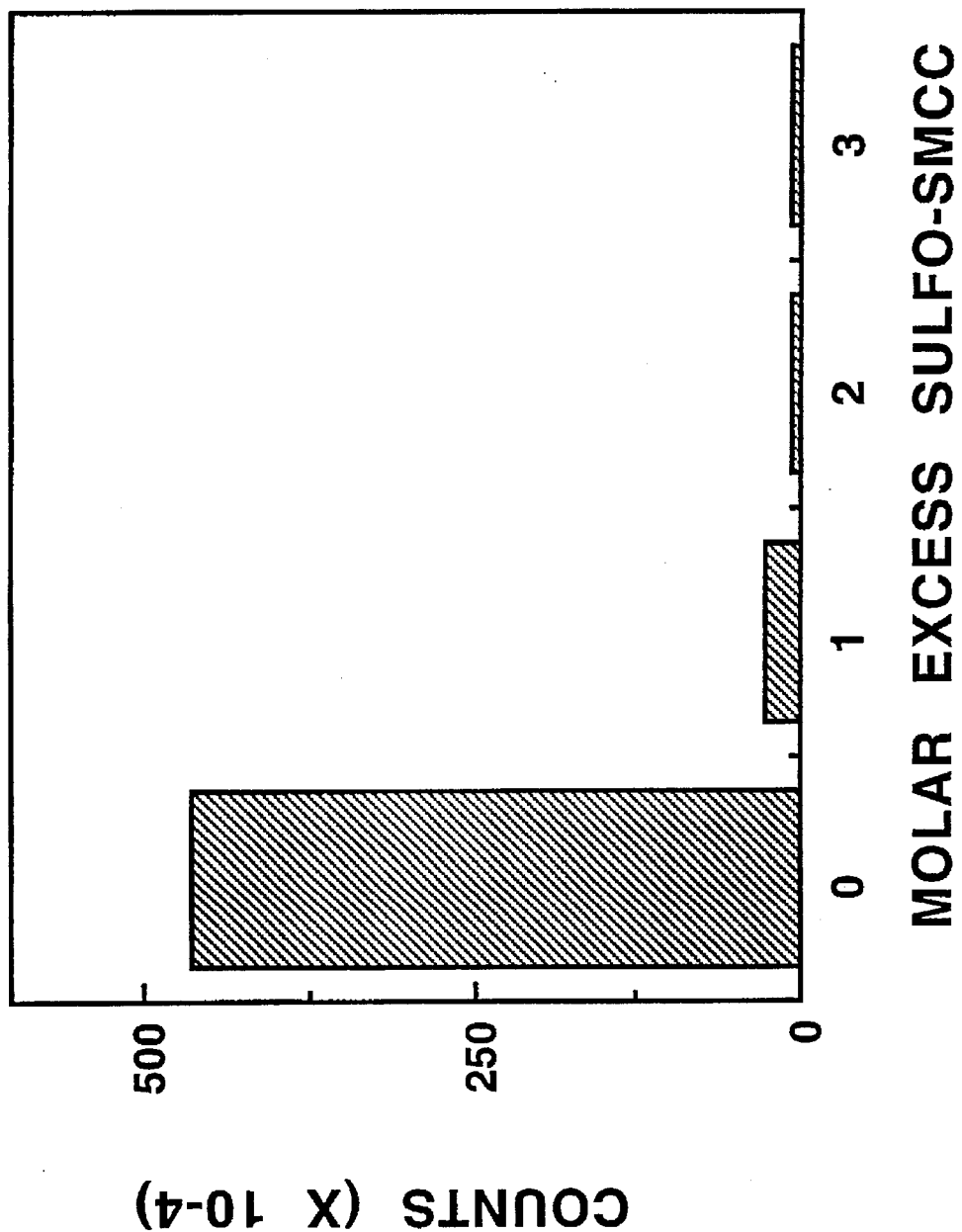
FIG. 1 is a graphic illustration of the inactivation of aequorin by treatment with increasing amounts of sulfo-SMCC as measured by the amount of light produced.

Important terms used in the specification are defined as follows:

The term "photoprotein" as used herein means any bioluminescent protein, i.e. any protein that is capable of producing light or which is a component of a luminescent reaction (i.e. a bioluminescent protein-mediated reaction that generates light). The term "photoprotein" includes bioluminescent enzymes such as luciferases and photoproteins such as aequorin. Examples of photoproteins include, but are not limited to, apoaequorin, aequorin, apo-obelin, obelin, apo-mnemiopsin, mnemiopsin, apo-berovin, berovin, pholasin, and the bioluminescent proteins isolated from the organisms Pelagia, ostracods such as Cypridina, and *Renilla luciferase*. Apo- forms of the photoproteins indicate that the protein is not bound to luciferin. In contrast, the non-apo- forms of the photoproteins indicate that luciferin is bound to the protein.

The term "apoaequorin," as used herein, means any of the related amino acid sequences commonly known in the art as apoaequorin sequences, including recombinant apoaequorin, as exemplified by Prasher et al. (1987), Sequence Comparisons of Complementary DNAs Encoding Aequorin Isotypes, *Biochemistry*, volume 26, number 5 1326–1332, which is hereby incorporated by reference. The term "apoaequorin" also is intended to encompass modified proteins, such as those altered by site-directed mutagenesis. Apoaequorin refers to the protein sequence alone without luciferin being tightly associated to form an aequorin complex.

The term "aequorin" as used herein means a complex formed of either naturally derived or recombinant apoaequorin protein to which luciferin and oxygen is bound. This complex is capable of producing light when triggered by a divalent cation such as calcium. The term "sulfhydryl-activated photoprotein" as used herein means a photoprotein as defined above that is chemically modified to contain at least one sulfhydryl group more than is present in the unmodified photoprotein.

The term "binding reagent," as used herein, means a compound capable of binding specifically to an analyte to be assayed that has amino groups available for chemical modification. The analyte to be assayed may be any selectively bindable material. Examples of binding reagents include, but are not limited to, streptavidin/avidin, lectins, enzymes, glycoproteins, peptides, hormones, receptors, antigens, drugs, antibodies and antigen binding fragments thereof, RNA, DNA, oligonucleotides, or any other selectively bindable molecules or compositions.

The term "sulfhydryl-activated" or "sulfhydryl-activated photoprotein," as used herein, means a photoprotein that has been modified to contain at least one sulfhydryl group in addition to the naturally occurring endogenous sulfhydryl groups in the photoprotein. Sulfhydryl-activated photoproteins can be reacted with sulfhydryl-reactive binding reagents to form the conjugates of the present invention.

The term "sulfhydryl-reactive" or "sulfhydryl-reactive binding reagent," as used herein, means a binding reagent capable of reacting with a sulfhydryl group on a sulfhydryl-activated photoprotein to form a photoprotein-binding reagent conjugate. One class of sulfhydryl-reactive binding reagents are those that have been modified to contain a maleimido group, and are termed "maleimido-activated." Another class of sulfhydryl-reactive binding reagents are those that have been modified to contain an α-halocarbonyl group.

The term "photoprotein-binding reagent conjugate" or "conjugate," as used herein, means a conjugate of a photoprotein and a binding reagent, as defined above, that are covalently coupled through a sulfhydryl-based crosslinking reaction.

The present invention encompasses a method of synthesis of conjugates of photoproteins with a variety of binding proteins including streptavidin/avidin, lectins, hormones, antigens, drugs, antibodies and antigen binding fragments thereof, or any other binding reagent by chemical crosslinking means. The present invention also encompasses photoprotein-binding reagent conjugates produced by this method.

The conjugation method of the present invention includes the steps of introducing additional sulfhydryl groups into a photoprotein to be conjugated, chemically modifying a binding reagent to render it sulfhydryl-reactive, and reacting the sulfhydryl-activated photoprotein with the sulfhydryl-reactive binding reagent to form the photoprotein-binding reagent conjugates of the present invention. The method yields stable photoprotein-binding reagent conjugates that retain luminescent activity.

While not wanting to be limited to this theory, it is postulated that the sulfhydryl activation of the photoprotein serves to protect endogenous sulfhydryl groups that are essential for bioluminescent activity. The subsequent crosslinking to a binding reagent via sulfhydryl groups in the sulfhydryl-activated photoprotein, does not, therefore, substantially adversely affect bioluminescent activity. This is a substantial improvement over the prior art conjugates of non-sulfhydryl-activated photoproteins.

Photoproteins used within the present invention include, but are not limited to, apoaequorin, aequorin, obelin, mnemiopsin, berovin, pholasin, luciferases, and the photoproteins isolated from Pelagia, Cypridina, and ostracods. A preferred photoprotein is aequorin or apoaequorin.

Photoproteins are sulfhydryl activated by chemical modification with appropriate reagents to add at least one more sulfhydryl group than is present on the unmodified photoprotein. Preferably multiple sulfhydryl groups are added to the photoprotein. Examples of such sulfhydryl activating reagents include, but are not limited to, 2-iminothiolane (Traut's reagent), N-succinimidyl S-acetyl thioacetate which is followed by deprotection with hydroxylamine. Additionally, S-acetylmercaptosuccinic anhydride (SAMSA), N-succinimidyl-3(2-pyridyl dithio) propionate (SPDP) and derivatives thereof being sulfonated or having an extended spacer arm, or 4-succinimidylozycarbonyl α-methyl α(2-pyridyldithio)toluene (SMPT), can be used, each of which is deprotected by treatment with a reducing agent. A preferred sulfhydryl activating reagent is 2-iminothiolane.

Binding reagents that can be used within the present invention include, but are not limited to, streptavidin/avidin, lectins, enzymes, glycoproteins, peptides, hormones, receptors, antigens, drugs, antibodies, RNA, DNA, oligonucleotides, or any other selectively bindable molecules or compositions by chemical crosslinking means. Preferred binding reagents are antibodies and antigens.

Binding reagents are chemically modified to make them sulfhydryl-reactive. Sulfhydryl-reactive heterobifunctional crosslinking reagents and sulfhydryl-reactive homobifunctional crosslinking reagents are used for this purpose.

Examples of heterobifunctional reagents that introduce maleimide groups include, but are not limited to, succinimidyl 4-(N-maleimidomethyl) cyclohexane (SMCC), sulfosuccinimidyl 4-(N-maleimidomethyl) cyclohexane-1-carboxylate (sulfo-SMCC), m-maleimido benzoyl-N-hydroxy succinimide ester (MBS) and the sulfonated derivative of MBS (sulfo-MBS), succinimidyl 4-(p-maleimidophenyl) butyrate (SMPB) and the sulfonated derivative thereof, (sulfo-SMPB), N-γ-maleimidobutyryloxysuccinimide ester (GMBS), sulfonated GMBS (sulfo-GMBS), succinimidyl-6-(N-maleimidohexanoate) (MHS), and long chain derivatives of these cross-linkers having extended linker arms. A preferred reagent is succinimidyl 4-(N-maleimidomethyl) cyclohexane-1-carboxylate (SMCC) and its sulfonated derivatives.

Examples of heterobifunctional reagents useful to introduce α-halocarbonyl groups include, but are not limited to, succinimidyl (4-iodoacetyl) aminobenzoate (SIAB), and the sulfonated derivative thereof (sulfo-SIAB), and N-hydroxy succinimidyl bromoacetate (HSBA).

Examples of homobifunctional reagents useful for sulfhydryl reactive crosslinking include, but are not limited to, bis (maleimido)-methyl ether (BMME) and bismaleimido hexane (BMH).

In a preferred embodiment of the invention, recombinant aequorin is chemically modified with 2-iminothiolane, rendering it sulfhydryl-activated. Separately, a binding reagent such as an antibody capable of binding specifically to the analyte to be assayed is chemically modified with the heterobifunctional crosslinker SMCC or sulfo-SMCC to render the binding reagent sulfhydryl-reactive. Subsequently, the sulfhydryl-activated photoprotein and sulfhydryl-reactive binding reagent are reacted under conditions sufficient to promote coupling to form a photoprotein-binding reagent conjugate.

The resulting conjugates optionally may be separated from the unreacted components of the reaction mixture by means commonly known to one skilled in the art. For example, the photoprotein-binding reagent conjugates generally will be appreciably larger in size than either the photoprotein or binding reagent alone. They easily can be purified, therefore, by separation over a chromatography column that separates components of a complex mixture based on their size. Additionally, conjugates may be separated by other means such as ion-exchange chromatography. Such separation techniques are well known in the art.

The photoprotein-binding reagent conjugates of the present invention may be used in a variety of binding assays to determine the presence or amount of analyte capable of being selectively bound to by a binding reagent. Examples of binding assays include sequential capture assays (also known as sandwich assays), simultaneous capture assays, competitive assays, and nucleic acid hybridization such as oligonucleotide binding to DNA or RNA. While such assays generally are termed binding assays, they may be termed immunoassays when antibodies are involved.

In one embodiment, assays of the present invention are conducted by contacting a photoprotein-binding reagent conjugate capable of binding an analyte, with a sample suspected of containing the analyte to be o determined, allowing the conjugate and analyte to bind together to form a photoprotein-binding reagent-analyte complex, separating the complex from the rest of the sample, and determining the presence or amount of analyte by initiating a luminescent reaction with the photoprotein and measuring the light produced.

Alternatively, the presence and amount of an analyte can be determined in a competitive binding assay wherein a sample with an unknown amount of analyte is combined with a known amount of an analyte-photoprotein conjugate, and the mixture allowed to bind to a limited amount of the binding partner for the analyte. The analyte-photoprotein conjugate competes with the analyte in the sample for binding to the analyte binding partner. The amount of conjugate that binds to the analyte binding partner is determined by initiating the luminescent reaction and measuring the light emitted. The amount of analyte in the sample is then determined as a function of the amount of competitive binding that occurred.

Many diagnostic assays utilize immunoassay techniques, and photoprotein-binding reagent conjugates of the present invention can be prepared where the binding reagent is an antibody. The antibody selected may be either monoclonal or polyclonal, and is capable of binding specifically to the analyte to be assayed. A sample to be assayed, for example, a body fluid, is contacted with a capture reagent, often an antibody, that is immobilized to a solid substrate such as a microtiter well. Analyte in the sample is selectively captured by the capture reagent and non-binding sample is washed away. Subsequently, photoprotein-antibody conjugate is contacted with the captured analyte so as to specifically bind to it. Excess photoprotein-antibody conjugate is washed away. Alternatively, the capture assay is conducted by mixing all binding components simultaneously.

The amount of conjugate bound is determined by measuring amount of light emitted by the conjugate. In the case of aequorin, light production is triggered by the addition of a divalent cation such as calcium. The amount of conjugate determined is indicative of the amount of analyte present in the sample.

The above-described conjugate is an example of the conjugates encompassed by the present invention. Various other binding reagent reagents can be substituted for the antibody. For example, an antigen-conjugate is within the scope of the present invention and is useful in competitive assays for determining the amount of the unconjugated antigen in a sample. Similarly, the conjugates of the present invention encompass lectins as the binding reagent, and are useful for determining the amount and type of carbohydrate or glycoprotein present in a sample. Additionally, the conjugates of the present invention encompass receptors and ligands as the binding reagent, and are useful for determining the presence and amount of a ligand or receptor, respectively, in a sample. Still further, the conjugates of the present invention encompass streptavidin/avidin as the binding reagent, and are useful for determining the presence and amount of any biotinylated analyte. In a similar fashion, the conjugates of the present invention encompass DNA, RNA, and oligonucleotides as the binding reagent, and are useful for detecting the presence and amount of nucleic acid molecules in a sample by nucleotide hybridization methods known in the art.

Other assays and methods of use of the conjugates of the present invention will be apparent to one skilled in the art and are intended to be encompassed within the appended claims.

The present invention will be better understood in light of the following specific examples.

EXAMPLE 1

Prior Attempts that Failed to Make Useful Conjugates

Prior to the invention a number of different approaches for the synthesis of aequorin conjugates were tried. One such approach was the introduction of maleimido groups into aequorin using the heterobifunctional reagent sulfo-SMCC, which contains a primary amine reactive N-hydroxysulfosuccinimide and a thiol reactive maleimide. This strategy involves reaction of aequorin amino groups with the NHS ester portion of sulfo-SMCC, generating a maleimido-activated derivative which subsequently can be covalently coupled with available sulfhydryl groups on a coupling partner. Modification of amino groups per se is not deleterious to aequorin, as illustrated by the successful creation of a biotinylated aequorin derivative (Stults et al., 1992).

However, introduction of maleimido groups that can react with accessible sulfhydryl groups on the same or adjacent molecules would likely result in loss of photoprotein activity. At least one of the three cysteine groups in aequorin has been shown to be essential for calcium dependent light production (Shimomura et al., 1978; Kemple et al., 1984). Site-directed mutagenesis studies have confirmed that all three cysteine groups play a role in aequorin activity (Tsuji et al., 1986; Kurose et al., 1989). One skilled in the art would expect, therefore, that chemical modification of critical sulfhydryl groups would significantly compromise the activity of aequorin.

Because at least one of the three cysteine residues in aequorin is involved in light production, and because the maleimido portion of sulfo-SMCC would react with the free sulfhydryl groups on aequorin during the activation step, one skilled in the art would expect a substantial reduction in aequorin light production activity. It was expected, therefore, that treatment of aequorin with sulfo-SMCC resulted in rapid inactivation of the photoprotein.

Aequorin was treated with up to a three fold molar excess of sulfo-SMCC for 30 minutes at room temperature. Light activity was monitored using a luminometer upon injection of calcium. The drastic and detrimental inactivation of aequorin by treatment with sulfo-SMCC is illustrated in FIG. 1. These results confirm the Erikaku et al. observation of rapid and substantial inactivation of aequorin by sulfo-SMCC activation.

In light of these considerations and the above-discussed results, it was not unexpected that the alternative coupling strategy using sulfo-SMCC, wherein the maleimido-activated coupling partner is reacted directly with the free sulfhydryls of aequorin, also yielded an unstable conjugate having little photoprotein activity. Table 1 illustrates the dramatic differences between conjugates made with unmodified aequorin and conjugates made using sulfhydryl-activated aequorin. Known amounts of thyroid stimulating hormone (TSH) were added to polystyrene tubes coated with a mouse monoclonal antibody against human TSH. Bound hormone was detected with an anti-human TSH mouse monoclonal antibody-aequorin conjugate prepared with aequorin which had been activated with 2-iminothiolane versus aequorin which was not sulfhydryl-activated. After washing, light activity was monitored using a luminometer upon injection of calcium.

TABLE 1

Use Of Antibody-Aequorin Conjugate For The Detection Of Tyroid Stimulating Hormone In A Simultaneous Capture Immuonassay.

| Conjugate | Specific Activity | μIU/TSH per ml | | |
|---|---|---|---|---|
| | | 0 | 0.5 | 50 |
| | (RLU/OD) | RLU Bound | | |
| Activated Aequorin | $4.2 \times 10^{11}$ | 232 (6.7) | 7163 (16.5) | 333368 (2.1) |
| Unmodified Aequorin | $3.1 \times 10^{10}$ | 266 (4.5) | 1603 (7.2) | 106068 (12.7) |

The unit μIU is micro International units of TSH, RLU means relative light units, RLU/OD means relative light units per optical density at 280 nm, and the number in parentheses is the %CV (coefficient of variation).

It is important to note that 6.5 fold more conjugate was required in the assays using conjugate prepared with unmodified aequorin. This data demonstrates that the performance of the conjugates synthesized with unmodified aequorin is very inferior to conjugates synthesized using aequorin modified to contain additional sulfhydryl groups. The specific activity of conjugates prepared without sulfhydryl addition is less than 10% compared to conjugates prepared with 2-iminothiolane. While the conjugate made with non-modified aequorin binds to TSH in an immunoassay, its performance is limited both in terms of immunoreactive RLU's, amount of IgG that has to be added, and the overall performance of the assay.

The discovery of modified and crosslinked aequorin-antibody conjugates that retained substantial luminescence was, therefore, a surprising and unexpected result. The highly photoactive aequorin-antibody conjugates of the present invention were synthesized as described below. The following non-limiting example is provided so that one skilled in the art can better understand the invention as defined by the appended claims.

EXAMPLE 2

Synthesis of Conjugates of Sulfhydryl-Activated Aequorin

Materials. 2-iminothiolane and sulfo-SMCC (sulfosuccinimidyl 4-(N-maleimidomethyl)cyclohexane-1-carboxylate) were obtained from Pierce Chemical Co. DEAE-Sepharose, Sephadex, Sephacryl, and all other chemicals were obtained from either Sigma Chemical Co. or Fisher Scientific. Light measurements were made using either a tube (Berthold Clinilumat LB9502) or microtiler plate (Dynatech ML1000 Microplate) luminometer. Opaque microtiter wells available from Dynatech (Microlite 2 wells) were used in the Dynatech instrument.

Figure 2:
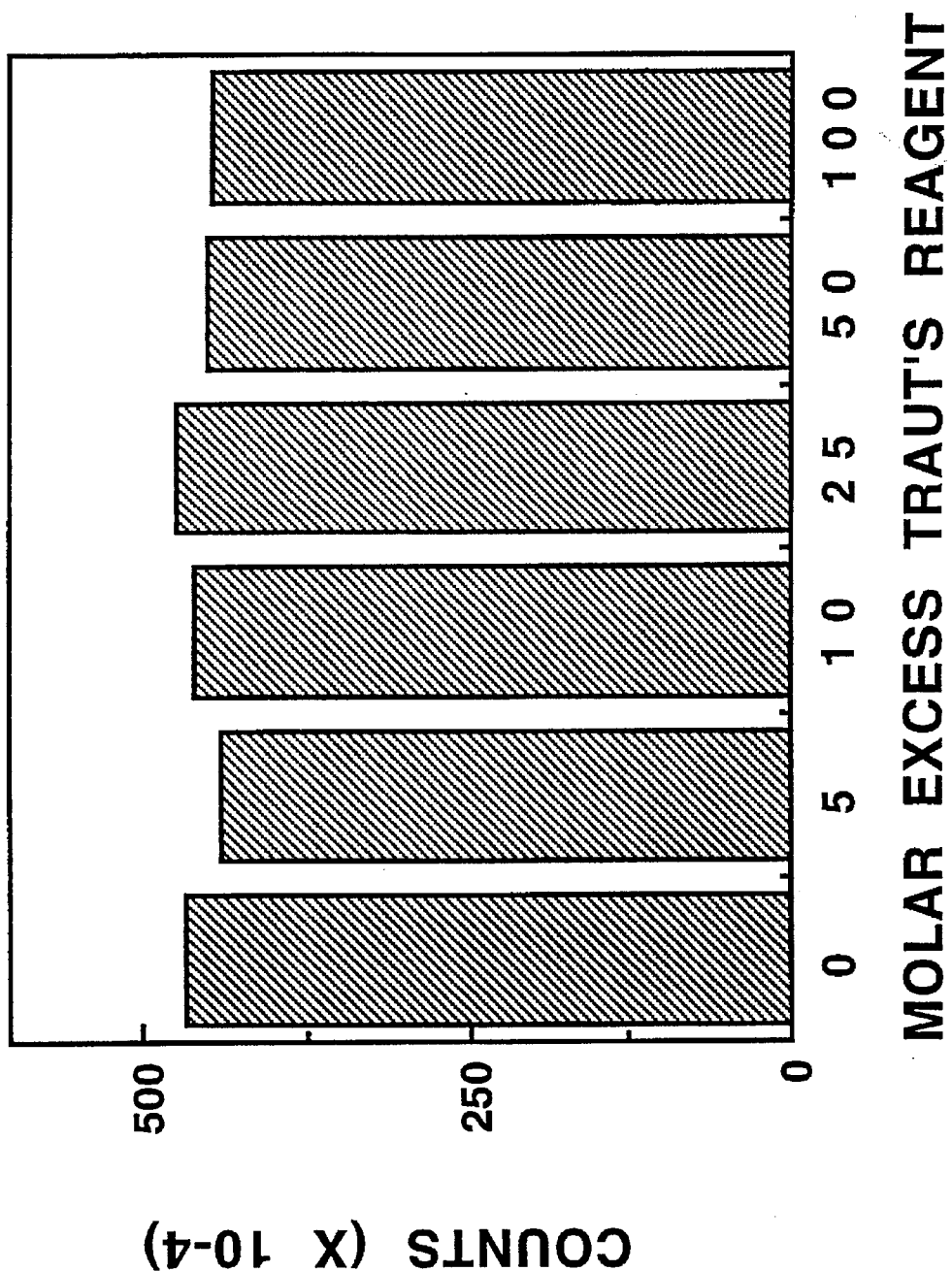
FIG. 2 is a graphic illustration of the lack of detrimental effect of 2-iminothiolane on aequorin as measured by the amount of light produced.

Activation of Aequorin with 2-iminothiolane. Aequorin, which is routinely stored in 10 mM Tris, 0.15M NaCl, pH 8.0 containing 2 mM EDTA (TBS/E), is exchanged into 0.1M sodium bicarbonate, 0.2M NaCl, 2 mM EDTA, pH 8.5 prior to activation with 2-iminothiolane by passing over a desalting column equilibrated in the bicarbonate buffer. One ml fractions are collected and the $O.D._{280}$ is monitored. The void fractions containing aequorin are pooled together and the amount of protein in the pooled fractions is estimated by $O.D._{280}$. Aequorin, which is now in the bicarbonate buffer, is then reacted with a 2-200 fold molar excess of 2-iminothiolane, by adding the appropriate volume of freshly prepared stock solution of 2-iminothiolane in bicarbonate buffer to the pooled aequorin. The solution is mixed gently and left at room temperature for 30 min. The reaction is stopped by adding excess amino reagent (50–100 μl of 1.5M Tris, pH 7–9). The reaction mixture is passed over a desalting column equilibrated in degassed 0.1M Tris, 2 mM EDTA, pH 7.0 (TE) to remove excess 2-iminothiolane. One ml fractions are collected and the $O.D._{280}$ is monitored. The void fractions containing the 2-iminothiolane activated-aequorin are combined and the amount of protein in the pooled fractions is estimated by $O.D._{280}$. The 2-iminothiolane activated-aequorin is stored on ice until it is combined with the maleimido-activated protein. FIG. 2 demonstrates that sulfhydryl activation of aequorin with 2-iminothiolane, even at a 100 molar excess, does not adversely affect aequorin light activity. Aequorin was treated with the amounts of 2-iminothiolane (Traut's reagent) indicated in FIG. 2 for 30 minutes at room temperature. Light activity was measured using a luminometer upon injection of calcium.

Activation of antibody. Binding reagents such as antibodies are routinely activated with a 5–50 fold molar excess of sulfo-SMCC. The antibody of interest, if lyophilized, is directly reconstituted in, or if in solution, exchanged by gel filtration, into 0.1M sodium bicarbonate, 0.2M NaCl, 0.5 mM EDTA, pH 7.5. The amount of antibody to be activated is determined by protein determination or by O.D.280 using the appropriate molar extinction coefficient. The appropriate volume of freshly prepared stock solution of sulfo-SMCC in bicarbonate is added to the antibody, the solution is mixed gently and allowed to react at room temperature for 30 min. The reaction is stopped by addition of Tris as described above and the reaction mixture is then passed over a desalting column equilibrated in degassed 0.1M Tris, 2 mM EDTA, pH 7.0 to remove excess sulfo-SMCC. The void fractions containing maleimido-activated antibody are combined and the amount of protein in the pooled fractions is determined from the $O.D._{280}$. The maleimido activated-antibody is stored on ice until it is combined with the 2-iminothiolane activated aequorin.

Conjugation and Conjugate Activity Assay. The 2-iminothiolane activated aequorin and sulfo-SMCC activated antibody are combined, usually at a molar ratio between 3 and 30, mixed gently, and allowed to react, without agitation, overnight at 4° C. To test for the presence of active antibody conjugate in the reaction mixture, aliquots are incubated in opaque microtiter wells or polystyrene tubes which have been coated with appropriate serum or purified anti-conjugate antibody or antigen which the aequorin-antibody conjugate will recognize or which will capture the conjugate or, in the case of streptavidin/avidin with a biotinylated target. For example, in the case of a mouse monoclonal antibody the microtiter wells can be coated with a goat anti-mouse immunoglobulin which will capture the conjugate. Typically, the wells or tubes are coated with 100 μl of 5–50 μg/ml of antibody overnight at 4° C. The coated wells or tubes are then blocked with an appropriate blocking reagent such as 1% gelatin/5 mg/ml BSA. A parallel set of blank wells or tubes are prepared by incubating untreated opaque microtiter wells with the same blocking reagent.

Several 10-fold dilutions of the conjugate reaction mixture are prepared in TBS/E containing 0.1 mg/ml BSA (TBS/E/BSA). Aliquots (100 μl/well) are placed into the blocked blank wells or tubes and blocked coated wells or tubes and allowed to incubate for 10 or more min at room temperature. The wells are washed 4–5 times with TBS/E to remove unbound conjugate. TBS/E/BSA (50 µl) is added to the wells or tubes to prevent drying. The microtiter wells or tubes are placed in an appropriate luminometer to monitor the presence of bound conjugate upon injection of calcium (10–100 mM Tris, 10–100 mM calcium acetate, pH 7.5). If a significant light signal is observed in wells or tubes coated with antibody/antigen/biotinylated target compared to blank wells or tubes, the conjugate is purified as follows.

Purification of Conjugate. Conjugates of aequorin with antibodies can be purified using a combination of gel filtration and ion-exchange chromatography. The order in which the purification steps are carried out does not matter with respect to the purified conjugate. Gel filtration is carried out using an appropriate resin (e.g., Sephadex G-100 or G-150, Sephacryl S-100 or S-200) which serves to separate free aequorin (MW 22,000) from the aequorin-antibody conjugate and any unreacted antibody present in the reaction mixture. An appropriate ion exchange media is used to remove unreacted antibody from the aequorin-antibody conjugate obtained after gel filtration. DEAE-Sepharose is routinely used which binds aequorin due to its acidic isoelectric point (pH~4.5). Aequorin-antibody conjugates are bound by the resin and require a salt gradient for elution. Binding reagents such as antibodies and streptavidin/avidin have more basic isoelectric points than aequorin, and will therefore either run through a DEAE column or will be bound with lesser affinity and will elute at a lower salt concentration.

Figure 4:
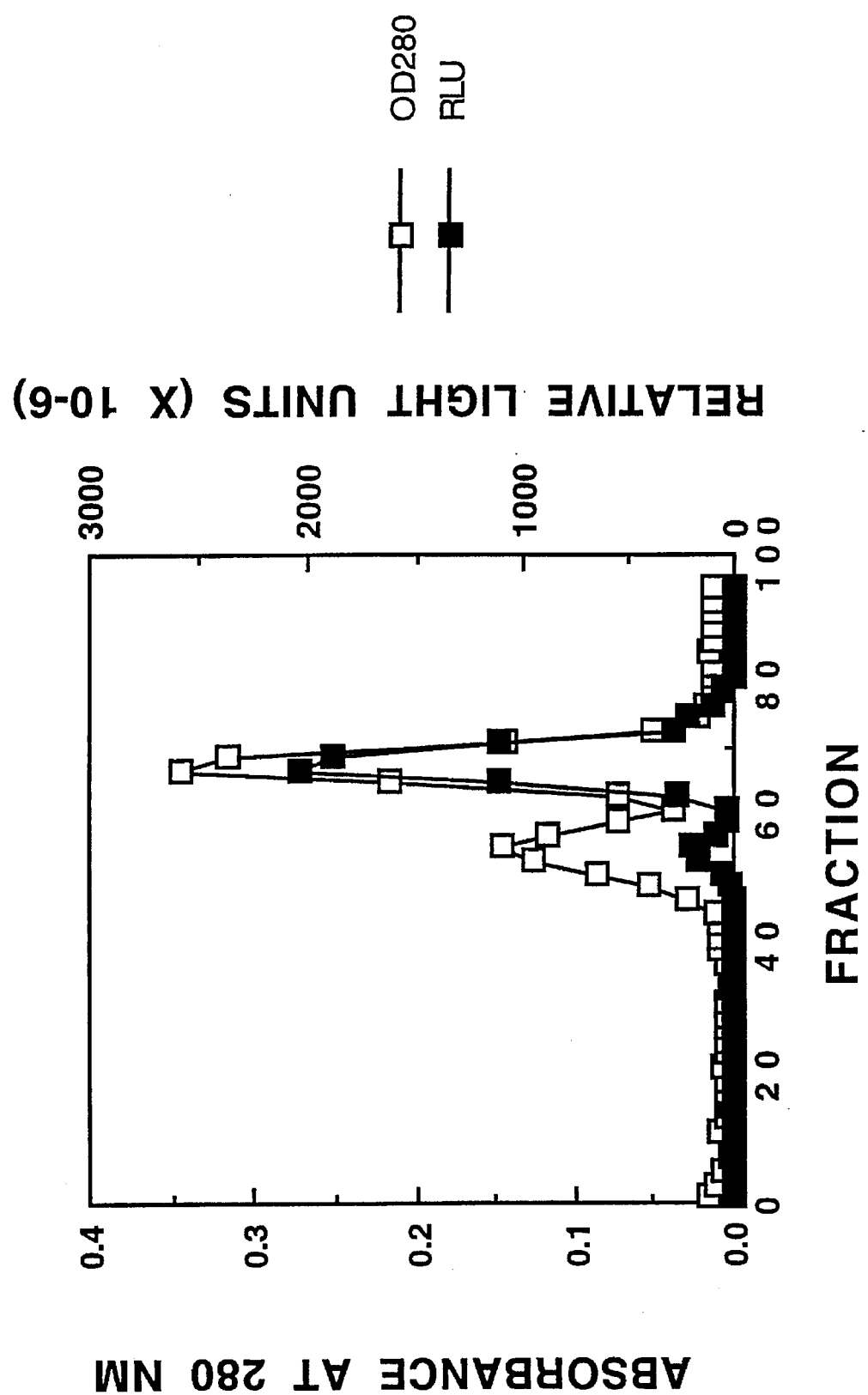
FIG. 4 is a gel-filtration chromatographic profile illustrating the purification of aequorin-antibody conjugates as measured by light production and O.D.$_{280}$ absorbance.

The conjugate reaction mixture is applied to the gel filtration column equilibrated in TE, pH 7.0. For example, a conjugate with antibody is applied to a Sephacryl S-200 column (1.2×85 cm) at 4° C. and the column is eluted with TE. Fractions (0.5–1.0 ml) are collected and monitored for the presence of light activity and protein by absorbance at 280 nm. The peak which elutes near the void volume of the column contains aequorin-antibody conjugate as well as unreacted binding reagent. The included peak of light activity corresponds to free aequorin. FIG. 4 illustrates a Sephacryl S-200 column chromatography purification profile of antibody-aequorin conjugate. One ml fractions were collected, protein concentration was measured spectrophotometrically at 280 nm, and light activity was measured using a luminometer upon injection of calcium.

The fractions which contain the aequorin-antibody conjugate are pooled and applied to a 5 ml DEAE-Sepharose column (1×12 cm) equilibrated with TE, pH 7.0. After washing the DEAE column with about 15–20 ml of TE, pH 7, proteins bound to the column are eluted using a linear salt gradient (50 ml total volume) with 25 ml of TE, pH 7 and 25 ml TE, pH 7 containing 0.6M NaCl. One ml fractions are collected and monitored for absorbance at 280 nm and light activity. Free antibody will be present in the first protein peak. The aequorin-antibody conjugate will be eluted later as a peak containing protein and light activity.

Figure 5:
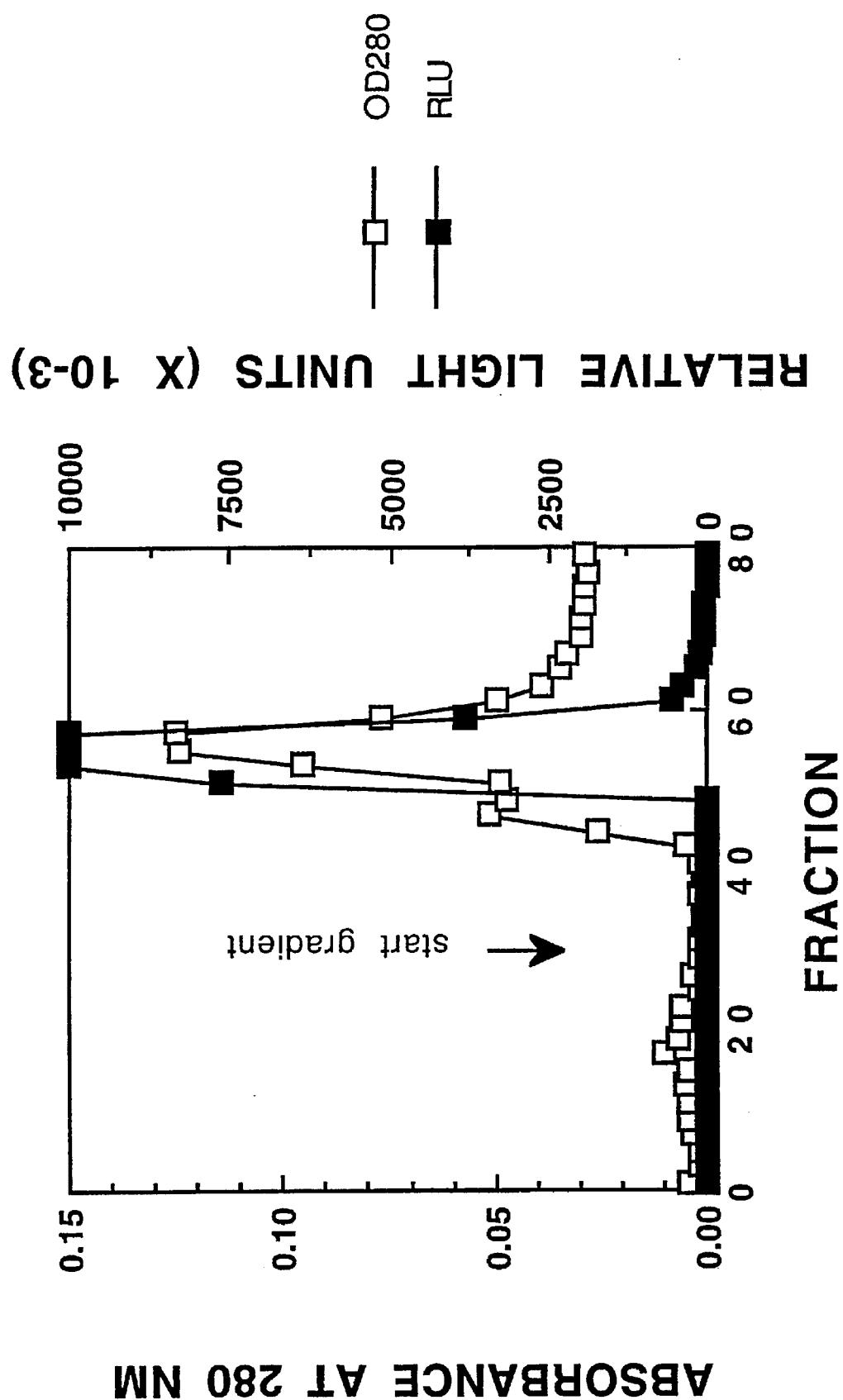
FIG. 5 is a DEAE ion-exchange chromatographic profile illustrating the purification of aequorin-antibody conjugates as measured by light production and optical density at 280 nm (O.D.$_{280}$).

FIG. 5 illustrates the elution profile of purification of antibody-aequorin conjugate by DEAE-Sepharose ion exchange chromatography. Light activity was measured using a luminometer upon injection of calcium. The fractions containing the purified aequorin-antibody are pooled and retested for the presence of active conjugate as described above. An aliquot of the purified conjugate is subjected to SDS-PAGE to further confirm the presence of conjugate. The specific activity (light activity per mg) of the conjugate is determined and the conjugate is stored under appropriate conditions.

EXAMPLE 3

Preparation of an Anti-Human TSH Antibody-Aequorin Conjugate

An anti-human TSH monoclonal antibody-aequorin reaction mixture, containing a 12 fold molar excess of sulfhydryl-activated aequorin over sulfo-SMCC maleimido-activated mouse anti-TSH antibody retained approximately 84% of its original light activity after overnight coupling at 4° C.

Figure 3:
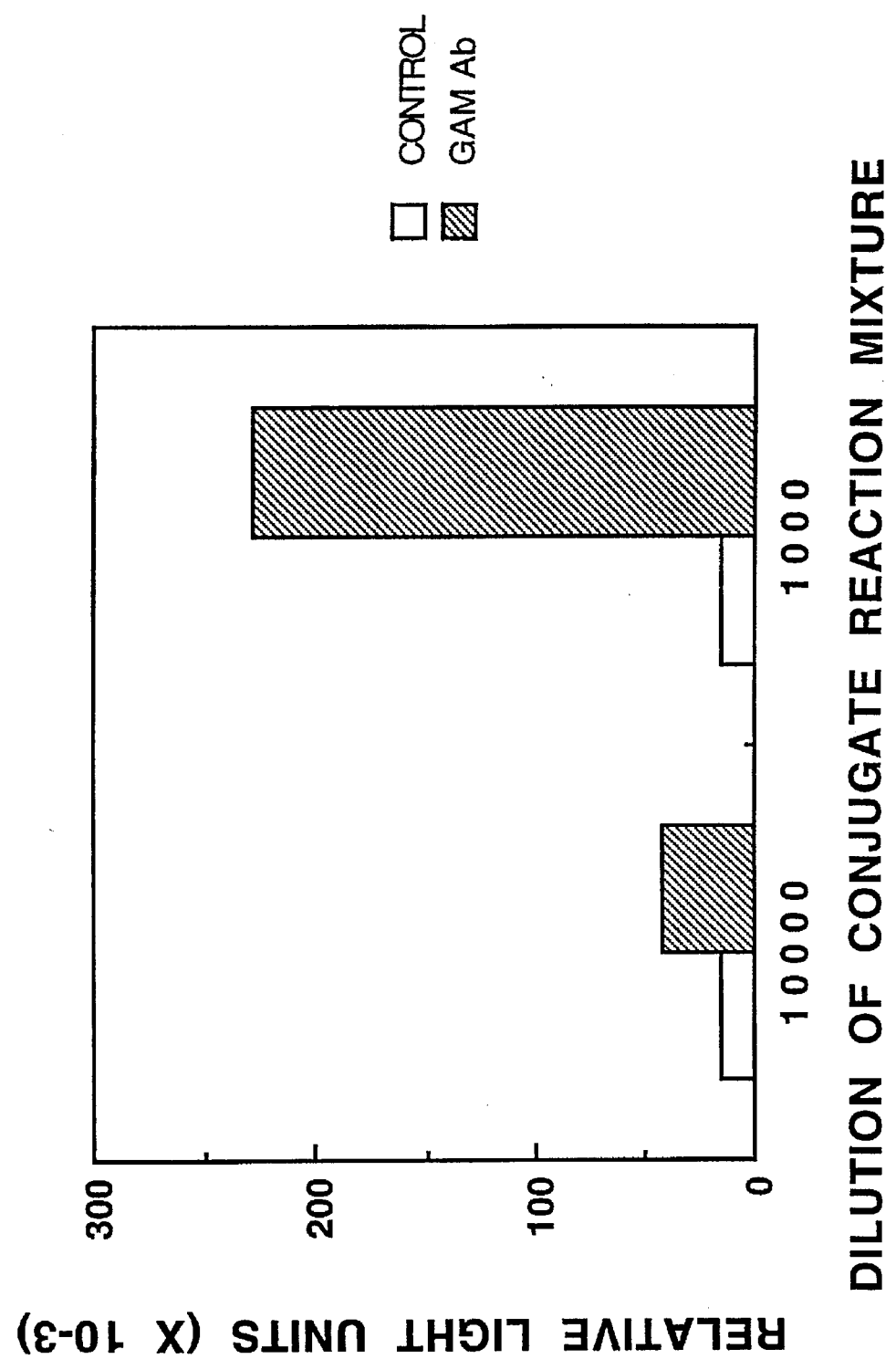
FIG. 3 is a graphic illustration of aequorin-(mouse antibody) conjugates binding specifically to immobilized goat anti-mouse antibody as measured by the amount of light produced.

The reaction mixture was shown to contain the desired conjugate based on the binding of 3–10 fold more light activity in microtiter wells that had been coated with goat anti-mouse antibody compared to wells that had been treated with blocking reagent only. Dilutions of conjugate were placed in opaque microtiter wells that were coated with goat anti-mouse antibody and treated with blocking reagent for 30 minutes at room temperature. Control microtiter wells were treated with blocking reagent only. After washing away unbound conjugates, bound light activity was determined using a microplate luminometer upon injection of calcium. The specific binding results are shown in FIG. 3.

The reaction mixture was placed over a Sephacryl S-200 column followed by DEAE-Sepharose ion exchange chromatography. The chromatographic profile is illustrated in FIG. 4. As shown in FIG. 4, approximately 6% of the light activity and 36% of the protein applied to the S-200 column was eluted near the void volume while the remaining light activity eluted in a position corresponding to free aequorin. The DEAE step served to remove traces of unconjugated antibody as shown in FIG. 5.

Coupling was confirmed by reducing SDS-PAGE analysis of the purified conjugate in which several bands of molecular weight greater than the antibody heavy chain (50 kD) were observed, data not shown. In addition, the same conjugate was stable in solution and to lyophilization with respect to both photoprotein and immunological activity. The conjugate retained approximately 70% of its light activity after storage in an appropriate buffer for one month at 4° C. and greater than 85% of its light activity when stored as a lyophilized powder at room temperature.

EXAMPLE 4

Thyroid Stimulating Hormone Binding Assay

A thyroid stimulating hormone (TSH) assay was performed. Briefly, known amounts of thyroid stimulating hormone (TSH) were added to polystyrene tubes coated with a mouse monoclonal antibody against human TSH. Bound hormone was detected with an anti-human TSH mouse monoclonal antibody-aequorin conjugate. After washing, light activity was monitored using a Berthold Clinilumat luminometer. As shown in Table 2, the anti-TSH antibody-aequorin conjugate was functional as demonstrated by the ability to detect low levels of TSH in a capture immunoassay.

TABLE 2

Use Of Antibody-Aequorin Conjugate For The Detection Of Thyroid Stimulating Hormone In A Simultaneous Capture Immunoassay.

| TSH µIU/ml | Relative Light Units (RLU) | % CV |
|---|---|---|
| 0 | 137 | 5.1 |
| 0.1 | 2458 | 1.2 |
| 50.0 | 658782 | 2.7 |

µIU = micro International units of TSH.

EXAMPLE 5

Competitive Immunoassay

A competitive immunoassay for thyroxine using thyroxine-(T4) aequorin conjugate was performed. Known amounts of thyroxine (T4) were added to polystyrene tubes coated with a donkey antibody against mouse IgG containing buffer with both a mouse antibody against thyroxine (T4) and a thyroxine-(T4) aequorin conjugate. After washing, bound conjugate was determined upon detection of calcium using a luminometer. The resulting competitive binding curve is shown in FIG. 6.

Additional experimental data indicate that reagents other than Traut's reagent and SMCC and sulfo-SMCC, which use the same chemistry, may be used for the preparation of active calcium-dependent photoprotein conjugates. These data demonstrate the universal nature of the sulfhydryl/maleimide conjugation strategy for photoproteins to yield conjugates possessing substantial bioluminescent activity. Further, data from experiments with the calcium-dependent photoprotein obelin indicate that the conjugation strategy can be successfully applied to recombinant obelin and other calcium-dependent photoproteins.

I. Maleimide/Sulfhydryl Conjugation Chemistry

The precise nature of the activating reagents is not critical for preparation of active calcium-dependent photoprotein conjugates, what is important is the nature of the functional moieties on such activating reagents. A variety of reagents may be used as long as the same sulfhydryl/maleimide coupling chemistry is maintained. In addition to Traut's reagent (2-iminothiolane) and SMCC (succinimidyl 4-[N-maleimidomethyl]cyclohexane-1-carboxylate) or its sulfonated derivative (sulfo-SMCC), similar reagents may be used to sulfhydryl activate aequorin and maleimido activate the binding partner (i.e., antibody, streptavidin, etc.), respectively.

A. Sulfhydryl Activation of Aequorin

Traut's reagent (a cyclic thiol-containing imidoester) reacts with primary amines to introduce sulfhydryl groups via lysine ε-amino groups or N-terminal α-amino groups at pH 7–10. The thiol-containing succinimidyl derivatives SPDP (N-succinimidyl pyridyldithiopropionate), SMPT (succinimidyl pyridyldithiopropionate), and SAMSA (S-acetylmercaptosuccinic anhydride) also react with primary amines in the same pH range. One skilled in the art who has read this disclosure would have a reasonable expectation that the thiol-containing succinimidyl derivatives have similar reactivities with aequorin amino groups, and would similarly introduce additional sulfhydryl moieties to the photoprotein.

Sulfhydryl aequorin was prepared using SPDP and SMPT derivatives which introduce a protected sulfhydryl group (as a disulfide bond) which requires treatment with a reducing agent (e.g., mercaptoethanol (MCE) or dithiothreitol (DTT)) to expose the added sulfhydryl group(s). Specifically, SMPT (4-succinimidyloxycarbonyl methyl-α-[2-pyridyldithio] toluene), LC-SPDP (succinimidyl 6-[3-[2-pyridyldithio] propionamido]hexanoate), and Sulfo-LC-SMPT (sulfosuccinimidyl 6-[α-methyl-α-(2-pyridyldithio) toluamido]hexanoate) was used to prepare active aequorin conjugates. It was found that all three reagents rapidly inactivated aequorin when used directly, presumably due to reaction of essential sulfhydryls on aequorin with the disulfide bridges in these reagents. However, this problem was circumvented by inclusion of DTT in the activation reaction to provide simultaneous deprotection. It was not anticipated that simultaneous deprotection by treatment with a reducing agent would be required to obtain active conjugates. Treatment of aequorin with 5 fold molar excess reagent in the presence of 5 mM DTT for 30 min at room temperature in Hepes buffered saline containing 2 mM EDTA, pH 8.0 preserved photoprotein activity and provided additional reduced sulfhydryl groups which are unprotected (i.e. ready to use in a conjugation reaction). After desalting the reaction mixtures, the incorporation of additional sulfhydryl groups in addition to those normally present in aequorin was confirmed using Ellman's reagent, which gave the following results: SMPT-1.2 mol, LC-SPDP-0.7 mol, and Sulfo-LC-SPDP-1.5 mol additional SH groups/mol aequorin.

To evaluate whether aequorin sulfhydryl activated with the three reagents mentioned above could be used for the preparation of active conjugates, aequorin streptavidin conjugates were prepared using SMCC activated streptavidin. Streptavidin was activated with a 2.5 fold molar excess of SMCC for 45 min at room temperature in Hepes buffered saline containing 2 mM EDTA, pH 8.0 to introduce maleimido groups. The reaction was quenched by addition of excess lysine and the reaction mixture was desalted. The resulting maleimido-activated streptavidin was reacted with the various preparations of sulfhydryl activated aequorin using a 4–5 fold molar excess of aequorin over streptavidin. The conjugation reactions were conducted for 1 h at room temperature in Hepes buffered saline containing 2 mM EDTA, pH 7.0. After quenching the conjugation reactions with excess dithiothreitol, the reaction mixtures were placed on a Sephacryl S200HR column (2.5×95 cm) to effect separation of the conjugate from unreacted sulfhydryl aequorin and maleimido streptavidin. Peaks corresponding to the 1:1 conjugate of aequorin with streptavidin (MW approximately 82 kD) were tested for the ability to function in an immunoassay for thyroid stimulating hormone (TSH).

The bioluminescent TSH immunoassay was carried out by pipetting 200 μL of human TSH standards in equine serum into Nunc MaxiSorb Star Tubes coated with a monoclonal antibody directed against the β-subunit of human TSH. Biotinylated conjugate polyclonal antibody (100 μL at 0.3 μg/mL) directed against the whole human TSH molecule was then immediately added in assay buffer (50 mM Tris-HCl, 20 mM EGTA, 2 mM EDTA, 10 mM MgCl$_2$, 1M KCl, 0.1 mg/mL each of mouse and goat gamma globulin, 1 mg/mL bovine serum albumin, and 15 mM sodium azide, pH 7.5). After a 2 h incubation at room temperature with rotation (180 rpm), the tubes were then washed in an automated tube washer using wash buffer (20 mM Tris-HCl, 0.15M NaCl, 5 mM EDTA, 0.5% Tween 20, 15 mM sodium azide, pH 7.0).

The complex of captured TSH and biotinylated antibody was detected by adding 200 μL of aequorin streptavidin conjugate in assay buffer containing 0.5% Tween 20 (having 400,000–500,000 relative light units (RLU) per 20 μL) to the washed tubes for 30 min at room temperature with rotation. After washing the tubes, bound light activity was measured as Relative Light Units (RLU) for 2 seconds using a Berthold LB 952 luminometer upon injection of 300 μL of buffered calcium acetate trigger solution into each tube. The results of the comparison of four different streptavidin aequorin preparations in the bioluminescent TSH immunoassay is shown in Table 3. The positive control is that conjugate prepared with aequorin sulfhydryl activated with Traut's reagent. The data clearly indicate that the three "experimental" conjugates, i.e., those prepared with aequorin sulfhydryl activated with SMPT, Sulfo-LC-SMPT, and SPDP, are functional in a bioluminescent immunoassay and perform very similarly to the positive control conjugate. These results demonstrate that a variety of thiol-containing succinimidyl derivatives are useful for the sulfhydryl activation of aequorin for the preparation of conjugates.

TABLE 3

Comparison of Streptavidin Conjugates Prepared with Aequorin Activated with Various Sulfhydryl Reagents in a Bioluminescent Immunoassay for Thyroid Stimulating Hormone

| Streptavidin Conjugate with Aequorin activated with | TSH Calibrator µIU/mL[2] | Relative Light Units (RLU) | S/N[1] |
|---|---|---|---|
| Traut's Rgt | 0 | 320 (14.5)[3] | |
| | 0.1 | 1229 (2.2) | 3.8 |
| | 1.1 | 8558 (5.3) | 27 |
| | 30 | 211620 (0.1) | 661 |
| SMPT | 0 | 239 (23.6) | |
| | 0.1 | 880 (3.8) | 3.7 |
| | 1.1 | 6006 (4.7) | 25 |
| | 30 | 137905 (11.6) | 577 |
| Sulfo-LC SMPT | 0 | 328 (11.0) | |
| | 0.1 | 986 (7.2) | 3.0 |
| | 1.1 | 6846 (8.6) | 21 |
| | 30 | 183016 (7.2) | 558 |
| LC SPDP | 0 | 239 (8.8) | |
| | 0.1 | 1008 (9.1) | 4.2 |
| | 1.1 | 7008 (3.5) | 29 |
| | 30 | 189278 (2.7) | 792 |

[1]S/N is the signal to noise (zero calibrator) ratio
[2]µIU/mL is micro International Units per mL
[3]% coefficient of variation shown in parenthesis B. Maleimide Activation of Binding Partner One skilled in the art would reasonably expect that maleimide activation reagents such as SMCC and sulfo-SMCC, MBS and sulfo-MBS, SMPB and sulfo SMPB, GMBS, sulfo-GMBS, and long chain derivatives thereof, which are all from a family of heterobifunctional crosslinkers o having an N-hydroxysuccinimide ester and maleimide functional groups, could be successfully used in the present invention to produce photoprotein conjugates. The chemistry of the modification is very similar and conducted under similar conditions of pH and buffer composition. First, the NHS portion of the crosslinker reacts with lysine ε-amino groups or N-terminal α-amino groups on the protein at alkaline pH (7–9) to introduce a reactive maleimido group. In the second reaction, the maleimido group on the protein is reacted with available sulfhydryl groups primarily on cysteine residues present in the binding partner under slightly acidic to neutral pH (6.5–7.5). One skilled in the art would expect that such NHS ester-maleimide heterobifunctional crosslinkers would have similar reactivities with the proteins or peptides involved in the conjugation reaction.

Several different maleimide/succinimide heterobifunctional crosslinkers in addition to SMCC (succinimidyl 4-[N-maleimidomethyl]cyclohexane-1-carboxylate) were used for the maleimide activation of the conjugate binding partner including SMPB (succinimidyl 4-p-maleimidophenyl] butyrate), MBS (m-maleimido-benzoyl-N-hydroxysuccinimide ester), and GMBS (N-γ-maleimidobutyryloxysuccinimide ester). For each maleimide/succinimide heterobifunctional crosslinker streptavidin was treated with a 2.5 fold (1.75 fold for SMPB) molar excess reagent for 30 min at room temperature in Hepes buffered saline containing 2 mM EDTA, pH 8.0. The reactions were quenched by addition of excess lysine and then, after desalting the reaction mixtures, the incorporation of maleimido groups was confirmed using mercaptoethanolamine and Ellman's reagent (SMCC-1.4, SMPB-0.9, MBS-1.2, GMBS- 1.9 mol maleimido groups/mol streptavidin).

Aequorin streptavidin conjugates were then prepared with streptavidin maleimido activated with the three reagents mentioned above using Traut's activated aequorin. Sulfhydryl aequorin was activated with a 15 fold molar excess of Traut's reagent for 30 min at room temperature in Hepes buffered saline containing 2 mM EDTA, pH 8.0. The reaction was quenched by addition of excess lysine and the reaction mixture was desalted. The resulting sulfhydryl-activated aequorin was reacted with the various preparations of maleimide activated streptavidin using a 4–5 fold molar excess of activated aequorin over activated streptavidin. The conjugation reaction was conducted for 1 h at room temperature in Hepes buffered saline containing 2 mM EDTA, pH 7.0. After quenching the conjugation reaction with excess dithiothreitol, the reaction mixture was placed on a Sephacryl S200HR column (1.6 or 2.5×95 cm) to effect separation of the conjugate from unreacted sulfhydryl aequorin and maleimido streptavidin. The peaks corresponding to the 1:1 conjugates of aequorin with streptavidin (MW approximately 82 kD) were pooled and tested for their ability to function in the bioluminescent TSH immunoassay described above.

The specific light activities (Relative Light Units (RLU) per mg calculated based on an absorption coefficient of 3.4 for a 1 mg/mL solution of streptavidin at 280 nm) of the different streptavidin aequorin preparations were found to be very comparable (SMCC-1.6×10$^{12}$ RLU/mg, MBS-1.7×10$^{12}$ RLU/mg, SMPB-1.7×10$^{12}$ RLU/mg, GMBS-2.2×10$^{12}$ RLU/mg) which indicates that the resulting conjugates are very similar despite the use of different reagents to activate the streptavidin. The results of the comparison of the four different streptavidin aequorin preparations in the bioluminescent TSH immunoassay are shown in Table 4. In this experiment the positive control is that conjugate prepared with streptavidin maleimide activated with SMCC. The data clearly indicate that the three "experimental" conjugates, i.e., those prepared with streptavidin maleimido activated with SMPB, MBS, and GMBS, are functional in a bioluminescent immunoassay and perform similarly to the positive control conjugate. These results demonstrate that different maleimido activating reagents possessing both a N-hydroxysuccinimide and maleimido functional group may be used to maleimido activate binding partners for conjugation with aequorin.

TABLE 4

Comparison of Streptavidin Conjugates Prepared with Streptavidin Activated with Various Maleimido Reagent in a Bioluminescent Immunoassay for Thyroid Stimulating Hormone

| Streptavidin Conjugate with Streptavidin activated with | TSH Calibrator µIU/mL[2] | Relative Light Unit (RLU) | S/N[1] |
|---|---|---|---|
| SMCC | 0 | 179 (16.7)[3] | |
| | 0.1 | 958 (14.7) | 5.4 |
| | 50 | 265022 (8.0) | 1480 |
| SMPB | 0 | 147 (22.6) | |
| | 0.1 | 771 (10.2) | 5.2 |
| | 50 | 204177 (3.8) | 1389 |
| MBS | 0 | 110 (9.9) | |
| | 0.1 | 652 (10.2) | 5.9 |
| | 50 | 185981 (4.1) | 1691 |
| GMBS | 0 | 272 (17.6) | |
| | 0.1 | 1334 (3.4) | 4.9 |
| | 50 | 348600 (3.9) | 1282 |

[1]S/N is the signal to noise (zero calibrator) ratio
[2]µIU/ML is micro International Units per mL
[3]% coefficient of variation shown in parenthesis II. Other Calcium Dependent Photoproteins One skilled in the art recognizes that there exists a related group of calcium-activated photoproteins including those derived from Cnidaria including aequorin, halistaurin, obelin, and clytin (formerly called phialidin), from Ctenophora including mnemiopsin I, mnemiopsin II, and berovin and from Radiolaria including thalassicolin. This group of photoproteins utilizes the same catalytic mechanisms and possess similar biological activity. They are triggered by calcium to emit light at approximately 470 nm; they have similar molecular weights (21–28 kD); they are believed to contain a common organic substrate (coelenterazine) and molecular oxygen bound as a complex; and each catalyzes a single turnover event unlike conventional enzymes.

Sequence data on clytin and obelin indicate 62% homology with aequorin, with structural similarities to aequorin including identical calcium binding sites, an essential proline residue at the C-terminus, several conserved amino acid residues including tryptophan, cysteine, and histidine believed to be essential for bioluminescence, and similar molecular weights. Thus, one skilled in the art recognizes that it is highly probable that aequorin, obelin, and clytin have similar mechanisms for light production and therefore, the likelihood of the current conjugation strategy being successful for obelin and clytin is great.

Furthermore, it reasonable to predict from what is known about this family of calcium-dependent photoproteins that the other lesser studied photoproteins (halistaurin, mnemiopsins, berovin and thalassicolin) are highly homologous to aequorin and similarly require the participation of essential cysteine residues for catalytic activity. Thus, one skilled in the art who has read this disclosure will have a reasonable expectation that the disclosed conjugation strategy will work with these other calcium-dependent photoproteins.

To evaluate the applicability of the conjugation strategy to other calcium-dependent photoproteins, a conjugate of recombinant obelin was prepared with a polyclonal goat antibody against thyroid stimulating hormone (TSH). First, the recombinant apoobelin was charged with coelenterate luciferin under conditions similar for the charging of apoaequorin. Specifically, apoobelin was incubated in Tris buffered saline containing EDTA, pH 7.0 in the presence of a two fold molar excess of coelenterate luciferin, 5 mM DTT, and ambient oxygen overnight at 2°–8° C. (It should be noted that these conditions have not yet been optimized to give maximum specific activity; the specific activity obtained (Relative Light Units per mg) is approximately 100 fold less than obtained with charged aequorin).

The charged obelin was then sulfhydryl activated (15 fold molar excess Traut's reagent for 30 min at room temperature in Hepes buffered saline with EDTA, pH 8.0) with no detectable loss of photoprotein activity. Using Ellman's reagent, a doubling of sulfhydryl content upon activation was estimated by comparing the sulfhydryl content of underivatized obelin with obelin treated with Traut's reagent.

Figure 7A:
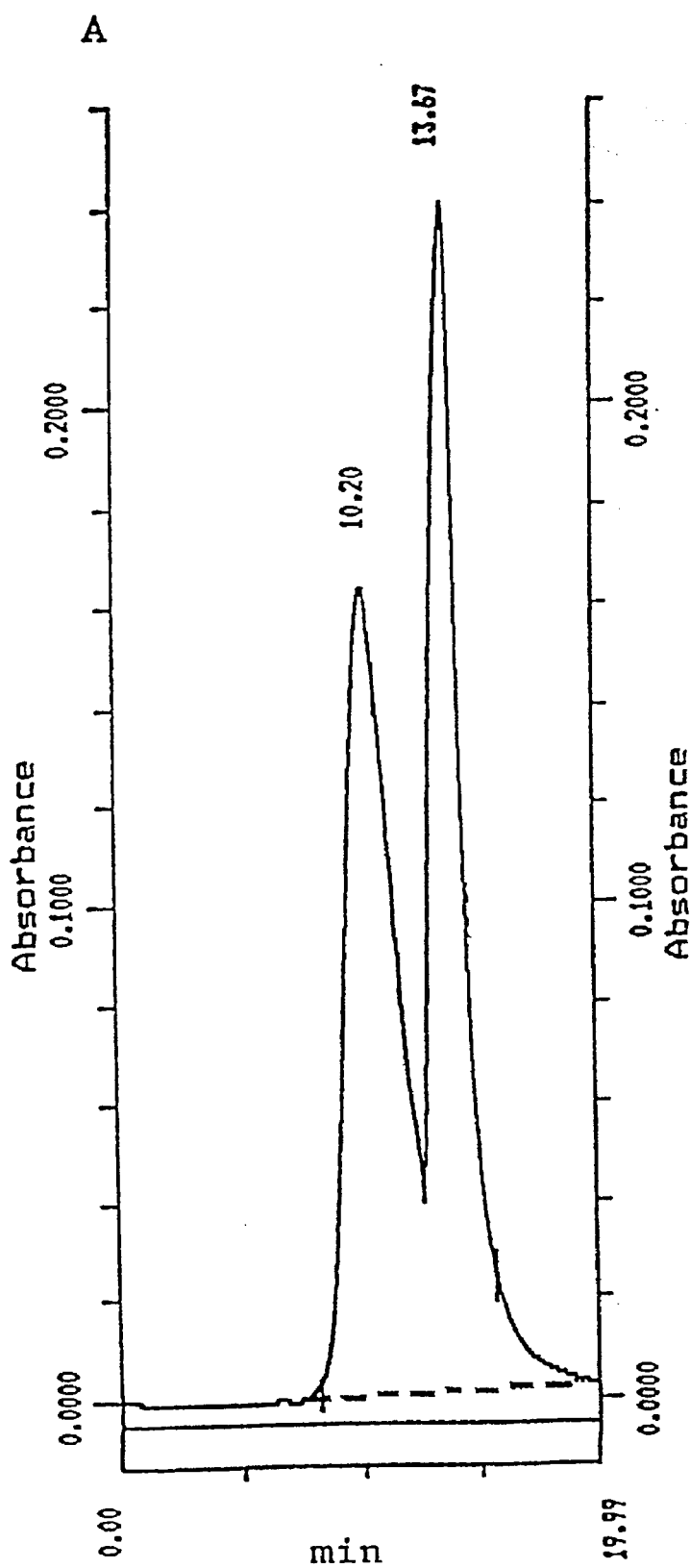
FIGS. 7A and 7B depict purification profiles of obelin anti-TSH antibody conjugate.
Figure 7B:
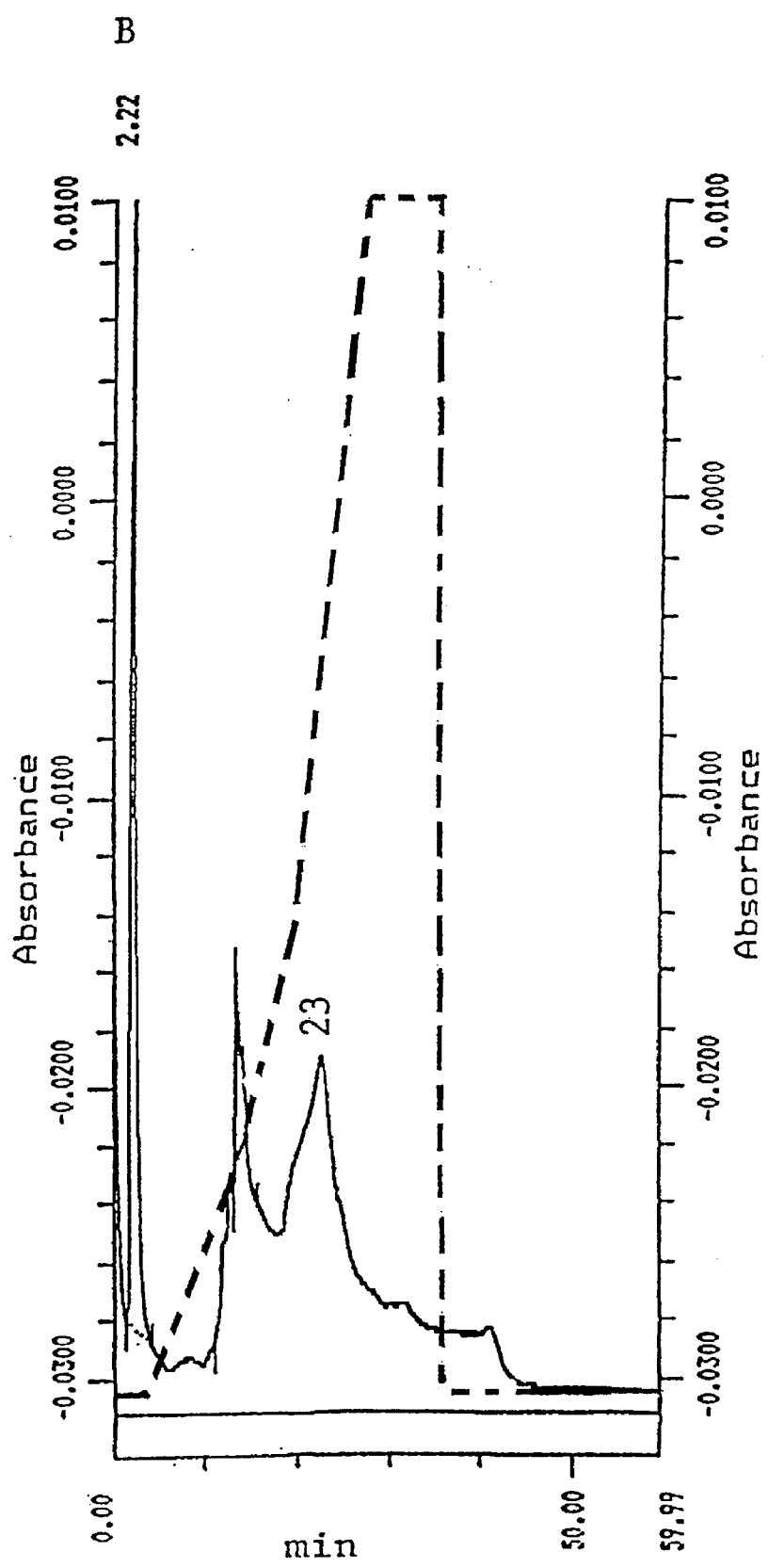

An anti-TSH polyclonal antibody obelin conjugate was then prepared by mixing the sulfhydryl activated obelin with maleimido activated goat anti-TSH polyclonal antibody. The conjugation reaction was conducted using a 2.5 fold molar excess of sulfhydryl activated obelin over SMCC activated anti-TSH antibody for 1 h at room temperature in Hepes buffered saline containing 2 mM EDTA, pH 7.0. The resulting conjugate was purified by HPLC using size exclusion to remove unreacted obelin followed by anion exchange on a DEAE column to remove unreacted antibody. The purification profiles shown in FIG. 7 are nearly identical to that obtained with the aequorin antibody conjugate described above. Panel A shows the size exclusion profile of the obelin anti-TSH antibody conjugate reaction mixture obtained on a Beckman SEC3000 (7.5mm×30 cm column) where the conjugate and unreacted antibody eluted at 10.2 min and unreacted obelin eluted at 13.7 min. Panel B shows the DEAE profile of the pooled obelin conjugate/free antibody peak from the SEC3000 column (10.2 min) obtained on a Beckman DEAE 5PW (7.5 mm×7.5 cm) column. A 0–600 mM salt gradient was run in 10 mM Tris, 2 mM EDTA, pH 7.5. The obelin anti-TSH antibody conjugate eluted at approximately 23 min while free antibody was not bound by the DEAE column and eluted at 2.2 min.

The purified obelin anti-TSH antibody conjugate was then evaluated in a simultaneous TSH assay. The assay was carried out by pipetting 200 μL of human TSH standards in equine serum into Nunc MaxiSorb Star Tubes coated with a monoclonal antibody directed against the β-subunit of human TSH. The anti-TSH polyclonal antibody conjugate of obelin or aequorin (100 μL at 400,000–450,000 relative light units (RLU) per 20 μL) was then immediately added in assay buffer (50 mM Tris-HCl, 20 mM EGTA, 2 mM EDTA, 10 mM $MgCl_2$, 1M KCl, 0.1 mg/mL each of mouse and goat gamma globulin, 1 mg/mL bovine serum albumin, and 15 mM sodium azide, pH 7.5). After a 2 h incubation at room temperature with rotation (180 rpm), the tubes were then washed in an automated tube washer using wash buffer (20 mM Tris-HCl, 0.15M NaCl, 5 mM EDTA, 0.5% Tween 20, 15 mM sodium azide, pH 7.0). After washing the tubes, the complex of captured TSH and obelin or aequorin labeled TSH antibody was then detected upon injection of 300 μL of buffered calcium acetate trigger solution into each tube using a Berthold LB 952 luminometer. The results are shown in Table 5 along with typical results obtained using the corresponding aequorin anti-TSH antibody conjugate in the same simultaneous TSH assay format.

TABLE 5

Performance of an Obelin Anti-TSH Conjugate in a
Simultaneous Bioluminescent Immunoassay for Thyroid
Stimulating Hormone
Relative Light Units (RLU) Bound

| TSH (μIU/mL)[1] | Obelin Anti-TSH Conjugate | Aequorin Anti-TSH Conjugate |
|---|---|---|
| 0.0 | 126 | 70 (1.6)[2] |
| 0.1 | 437 (1.0) | 1984 (1.7) |
| 0.5 | 1653 (1.1) | 8690 (7.1) |
| 5.3 | 16781 (7.6) | 86942 (5.3) |
| 10.6 | 32549 (0.1) | 162340 (5.4) |
| 50 | 213431 (1.3) | 554510 (0.7) |

[1] μIU/mL is micro International Units per mL
[2] % coefficient of variation shown in parenthesis The data in Table 5 show that a highly functional anti-TSH antibody conjugate can be prepared with obelin, even without any optimization for the different photoprotein, using the same sulfhydryl/maleimide chemistry used for the preparation of aequorin conjugates. While the signal is somewhat less than observed with the corresponding aequorin conjugate, the obelin conjugate demonstrates linearity and broad dynamic range. Since the charging reaction of obelin has not been optimized, it is likely that a significant proportion of the obelin anti-TSH conjugate actually consists of uncharged apoobelin, and therefore, it is reasonable and expected that the light signal generated by the unoptimized obelin conjugate would be lower than the light signal observed with the aequorin conjugate. The performance of the obelin conjugate would be expected to improve significantly upon optimization of the charging reaction of obelin, and of subsequent activation and conjugation reactions. These results demonstrate that the disclosed conjugation method of the present invention can be applied to the calcium-dependent photoprotein obelin, and other calcium-dependent photoproteins generally.

EXAMPLE 6

Preparation of Nucleic Acid Photoprotein Conjugates

In general DNA/RNA probes can be derivatized in manners similar to proteins. Complementary probes to specific sequences of RNA and DNA can be made and derivatized either directly through the amino terminal or side chain amino, carboxyl, or other functionality, or reacted with derivatizing agents to provide more active "labelable" groups. In addition DNA can be cross linked with materials such as psoralens that can provide free amine groups for attachment. Examples illustrating these methods follow.

Probes can be reacted with activators such as 1,1'-carbonyldiimidazole and a bis-amine to provide an aliphatic primary amine attachment for the probe that does not interfere with DNA double helix formation. The primary amine can then be reacted, as the oligonucleotide, with a NHS ester, such as Sulfo-SMCC, to add the maleimido function. Examples of this are shown in the paper by S. Beck, T. O'Keeffe, J. J. Coull, and H. Kuster. (Nuc. Acid. Res., 1989, 17, 5115–5123), which is incorporated by reference. While the modified oligo is reacted with NHS-biotin, it is substantially likely that SMCC could be used.

Alkyl amine linkers can be added either during synthesis of the probe or post synthesis. An example of this modification is the use of allyl amine. This will react with, for example, the C-5 position of pyrimidines to yield the allyl amine group which can be modified using standard NHS or other chemistry to attach a SMCC or equivalent group. See L. Gardner in BioTechniques, 1983, 38–41, and their use in PNAS, 1983, 80, 4045–4049, both of which are incorporated by reference.

Acridinium esters have been attached to amine modified DNA and RNA molecules using NHS chemistry to yield DNA and RNA probes. See L. J. Arnold Jr., in Clinical Chemistry, 1989, 35, 1588–94, which is incorporated by reference.

Such probes can be used in nucleic acid hybridization assays, such as oligonucleotides hybridizing to DNA or RNA, that are known in the art.

Having fully described the invention in the above description and examples, other variants and uses will be apparent to one skilled in the art. All such variations are intended to fall within the scope of the appended claims.

I claim:

1. A photoprotein-binding reagent conjugate composition comprising a sulfhydryl-activated photoprotein coupled to a maleimide activated binding reagent, said conjugate composition capable of emitting light.

2. The composition of claim 1, wherein said sulfhydryl-activated photoprotein is modified to contain at least one sulfhydryl group more than is present in an unmodified photoprotein, and wherein said maleimide activated binding reagent is modified so as to crosslink with at least one sulfhydryl group on said photoprotein.

3. The composition of claim 1 wherein said photoprotein is selected from the group consisting of apoaequorin, aequorin, apo-obelin, obelin, apo-mnemiopsin, mnemiopsin, apo-berovin, berovin, pholasin, clytin, halistovein thalassiciolin and bioluminescent proteins isolated from Pelagia, or ostracods.

4. The composition of claim 1 wherein said binding reagent is selected from the group consisting of streptavidin/avidin, lectins, enzymes, glycoproteins, peptides, hormones, receptors, antigens, drugs, antibodies and antigen binding fragments of said antibodies thereof, and RNA and DNA oligonucleotides.

5. The composition of claim 1 wherein said photoprotein is apoaequorin or aequorin and said binding reagent is an antibody.

6. The composition of claim 1 wherein said photoprotein is apoaequorin or aequorin and said binding reagent is an antigen.

7. The composition of claim 1 wherein said photoprotein is apoaequorin or aequorin and said binding reagent is a nucleic acid molecule.

8. The composition of claim 1 wherein said photoprotein is sulfhydryl activated with a sulfhydryl activating reagent selected from the group consisting of 2-iminothiolane (Traut's reagent); S-acetylmercaptosuccinic anhydride (SAMSA) followed by deprotection by treatment with a reducing agent; N-succinimidyl-3-(2-pyridyldithio) propionate (SPDP) and derivatives thereof, with simultaneous deprotection by treatment with a reducing agent; 4-succinimidylozycarbonyl α-methyl α (2-pyridyldithio)-toluene (SMPT) with simultaneous deprotection by treatment with a reducing agent; and derivatives thereof.

9. The composition of claim 8 wherein said photoprotein is sulfhydryl activated with 2-iminothiolane.

10. The composition of claim 1 wherein said binding reagent is maleimide activated by treating said binding reagent with a compound selected from the group consisting of succinimidyl 4-(N-maleimidomethyl) cyclohexane (SMCC), the sulfonated derivative of SMCC, m-maleimido benzoyl-N-hydroxy succinimide ester (MBS), the sulfonated derivative of MBS (sulfo-MBS), succinimidyl 4-(p-maleimidophenyl) butyrate (SMPB), the sulfonated derivative of SMPB (sulfo-SMPB), succinimidyl-6-(N-maleimide-n-hexanoate), N-γ-maleimidobutyryloxysuccinimide ester (GMBS), the sulfonated derivative of GMBS, bis-(maleimido) methyl ether, and bis-maleimido hexane (BMH) and long chain derivatives thereof.

11. The composition of claim 10 wherein said binding reagent is maleimide activated by treating said binding reagent with succinimidyl 4-(N-maleimidomethyl) cyclohexane-1-carboxylate (SMCC) or its sulfonated derivative (sulfo-SMCC).

12. A method of making a photoprotein-binding reagent conjugate composition comprising the step of coupling a sulfhydryl-activated photoprotein to a maleimide activated binding reagent, said conjugate composition capable of emitting light.

13. The method of claim 12, wherein said sulfhydryl-activated photoprotein is modified to contain at least one sulfhydryl group more than is present in the unmodified photoprotein, and wherein said maleimide activated binding reagent is modified so as to crosslink with a sulfhydryl group on said photoprotein.

14. The method of claim 12, wherein said photoprotein is selected from the group consisting of apoaequorin, aequorin, apo-obelin, obelin, apo-mnemiopsin, mnemiopsin, apo-berovin, berovin, pholasin, clytin, halistovein thalassiciolin and bioluminescent proteins isolated from Pelagia, or ostracods.

15. The method of claim 12 wherein said binding reagent is selected from the group consisting of streptavidin/avidin, lectins, enzymes, glycoproteins, peptides, hormones, receptors, antigens, drugs, antibodies and antigen binding fragments thereof, and RNA and DNA oligonucleotides.

16. The method of claim 12 wherein said photoprotein is apoaequorin or aequorin and said binding reagent is an antibody.

17. The method of claim 12 wherein said photoprotein is apoaequorin or aequorin and said binding reagent is an antigen.

18. The method of claim 12 wherein said photoprotein is apoaequorin or aequorin and said binding reagent is a nucleic acid molecule.

19. The method of claim 12 wherein said photoprotein is sulfhydryl activated with a sulfhydryl activating reagent selected from the group consisting of 2-iminothiolane (Traut's reagent); S-acetylmercaptosuccinic anhydride (SAMSA) followed by deprotection by treatment with a reducing agent; N-succinimidyl-3-(2-pyridyldithio) propionate (SPDP) and derivatives thereof, with simultaneous deprotection by treatment with a reducing agent; 4-succinimidylozycarbonyl α-methyl α (2-pyridyldithio)-toluene (SMPT) with simultaneous deprotection by treatment with a reducing agent; and derivatives thereof.

20. The method of claim 19 wherein said photoprotein is sulfhydryl activated with 2-iminothiolane.

21. The method of claim 12 wherein said binding reagent is maleimide activated by treating said binding reagent with a compound selected from the group consisting of succinimidyl 4-(N-maleimidomethyl) cyclohexane, (SMCC) the sulfonated derivative of SMCC m-maleimido benzoyl-N-hydroxy succinimide ester (MBS), the sulfonated derivative of MBS (sulfo-MBS), succinimidyl 4-(p-maleimidophenyl) butyrate (SMPB), the sulfonated derivative of SMPB (sulfo-SMPB), succinimidyl-6-(N-maleimide-n-hexanoate), bis-(maleimido) methyl ether, and bis-maleimido hexane (BMH).

22. The method of claim 21 wherein said binding reagent is maleimide activated by treating said binding reagent with succinimidyl 4-(N-maleimidomethyl) cyclohexane-1-carboxylate (SMCC) or its sulfonated derivative (sulfo-SMCC).

23. An assay method for determining the presence or amount of an analyte in a sample comprising the steps of contacting a photoprotein-binding reagent conjugate of claim 1 specific for an analyte with a sample suspected of containing the analyte to form a photoprotein-binding reagent-analyte complex, separating the complex from the rest of the sample mixture, initiating a luminescent reaction with either the bound or unbound photoprotein-binding reagent conjugate and measuring the light produced.

24. The assay method of claim 23 wherein the binding assay is selected from the group comprising simultaneous capture binding assays, sequential capture binding assays, competitive binding assays, and nucleic acid hybridization.

25. The assay method of claim 23 wherein the photoprotein-binding reagent conjugate capable of binding specifically to the analyte to be determined is contacted with the sample suspected of containing the analyte to be determined, under condition sufficient for the photoprotein-binding reagent conjugate and analyte to bind together to form a photoprotein-binding reagent-analyte complex, simultaneously or subsequently separating the complex from the rest of the sample, and determining the presence or amount of analyte by initiating a luminescent reaction with the photoprotein and measuring the light produced.

26. The assay method of claim 23 wherein the photoprotein-binding reagent conjugate specific for a binding partner of the analyte to be determined is contacted with the sample suspected of containing the analyte under conditions sufficient for the photoprotein-binding reagent conjugate and binding partner to bind together to form a photoprotein-binding reagent-analyte binding partner complex, subsequently separating the complex from the rest of the sample, and determining the presence or amount of analyte by initiating a luminescent reaction with the photoprotein and measuring the light produced.

* * * * *